(12) United States Patent
Atyabi et al.

(10) Patent No.: US 8,460,711 B2
(45) Date of Patent: Jun. 11, 2013

(54) POLY(CITRIC ACID) FUNCTIONALIZED CARBON NANOTUBE DRUG DELIVERY SYSTEM

(76) Inventors: Fatemeh Atyabi, Tehran (IR); Mohsen Adeli, Khoramabad (IR); Zahra Sobhani, Shiraz (IR); Rassoul Dinarvand, Tehran (IR); Mohammad Hossein Ghahremani, Tehran (IR)

( * ) Notice: Subject to any disclaimer, the term of this patent is extended or adjusted under 35 U.S.C. 154(b) by 310 days.

(21) Appl. No.: 12/870,943

(22) Filed: Aug. 30, 2010

(65) Prior Publication Data

US 2010/0324315 A1 Dec. 23, 2010

(51) Int. Cl.
*A61K 9/51* (2006.01)
*C07B 41/12* (2006.01)
*A61K 9/00* (2006.01)

(52) U.S. Cl.
CPC ............ *A61K 9/0092* (2013.01); *Y10S 977/752* (2013.01); *Y10S 977/906* (2013.01); *Y10S 977/742* (2013.01); *C07B 41/12* (2013.01)
USPC ........... 424/490; 977/742; 977/752; 977/906; 977/742

(58) Field of Classification Search
None
See application file for complete search history.

(56) References Cited

U.S. PATENT DOCUMENTS

| 5,767,113 | A * | 6/1998 | Cohn et al. | 514/176 |
| 2009/0087493 | A1 * | 4/2009 | Dai et al. | 424/490 |

OTHER PUBLICATIONS

M Adeli, A Bahari, H Hekmatara. "Carbon Nanotube-Graft-Poly(Citric Acid) Nanocomposites." Nano: Brief Reports and Reviews, vol. 3 No. 1, 2008, pp. 37-44.*
SC Tsang, YK Chen, PJF Harris, MLH Green. "A Simple Chemical Method of Opening and Filling Carbon Nanotubes." Nature, vol. 372, Nov. 10, 1994, pp. 159-162.*
B Neises, W Steglich. "Stimple Method for the Esterification of Carboxylic Acids." Angew. Chem. Int. Ed. Engl., vol. 17 No. 7, 1978, pp. 522-524.*

* cited by examiner

*Primary Examiner* — Frederick Krass
*Assistant Examiner* — Isaac Shomer (57) ABSTRACT

A method for synthesizing carbon nanotube drug carriers and the carbon nanotube drug carriers are disclosed. Initially, carbon nanotubes, nitric acid, and sulfuric acid are mixed to oxidize carbon nanotubes in a first mixture. The oxidized carbon nanotubes are then extracted from the first mixture. The oxidized carbon nanotubes and monohydrated citric acid are mixed to synthesize carbon nanotubes grafted with poly (citric acid) in a second mixture. The carbon nanotubes grafted with poly(citric acid) are then extracted from the second mixture. The carbon nanotubes grafted with poly(citric acid) and 4-(dimethylamino)pyridine are dissolved in anhydrous dimethylformamide in a third mixture. Next, a mixture that comprises a drug is added to the third mixture to synthesize the carbon nanotubes grafted with poly(citric acid) and the drug in a fourth mixture. Then, the carbon nanotubes grafted with poly(citric acid) and the drug are extracted from the fourth mixture.

13 Claims, 14 Drawing Sheets

POLY(CITRIC ACID) FUNCTIONALIZED CARBON NANOTUBE DRUG DELIVERY SYSTEM

SPONSORSHIP STATEMENT

This application has been sponsored by the Iranian Nanotechnology Initiative Council, which does not have any rights in this application.

TECHNICAL FIELD

This application generally relates to drug delivery, and more particularly relates to a drug delivery by means of poly(citric acid) functionalized carbon nanotubes.

BACKGROUND

The various properties of carbon nanotubes, such as, for example, their stability, inertness, and relatively high surface area-to-volume ratio, make them effective carriers for drug delivery. The application of carbon nanotubes in drug delivery was first studied after the discovery that carbon nanotubes could penetrate into cells. Since this discovery, several in vitro studies have shown that carbon nanotubes can transport drugs, peptides, and proteins into cells. The shapes and sizes of carbon nanotubes are critical factors that affect the efficiency of drug delivery systems.

However, the high hydrophobicity, low functionality, and large size of pristine carbon nanotubes limit their biological applications. As a result, carbon nanotubes have been modified through the covalent or noncovalent functionalization of their external walls to enable the linkage of a variety of active molecules to the walls of carbon nanotubes. Nevertheless, functionalized carbon nanotubes have not been effective carriers of small molecules, such as antiviral, antibacterial, and anticancer agents.

SUMMARY

A method for synthesizing carbon nanotube drug carriers and the carbon nanotube drug carriers are disclosed. Initially, carbon nanotubes, nitric acid, and sulfuric acid are mixed to oxidize carbon nanotubes in a first mixture. The oxidized carbon nanotubes are then extracted from the first mixture. The oxidized carbon nanotubes and monohydrated citric acid are mixed to synthesize carbon nanotubes grafted with poly(citric acid) in a second mixture. The carbon nanotubes grafted with poly(citric acid) are then extracted from the second mixture. The carbon nanotubes grafted with poly(citric acid) and 4-(dimethylamino)pyridine are dissolved in anhydrous dimethylformamide in a third mixture. Next, a mixture that comprises a drug is added to the third mixture to synthesize the carbon nanotubes grafted with poly(citric acid) and the drug in a fourth mixture. Then, the carbon nanotubes grafted with poly(citric acid) and the drug are extracted from the fourth mixture.

In some embodiments, the ratio of nitric acid to sulfuric acid in the first mixture can be 1 to 3. The carbon nanotubes, the nitric acid, and the sulfuric acid in the first mixture can be sonicated. The carbon nanotubes can be multi-walled carbon nanotubes. The first mixture can be diluted with distilled water to adjust the pH of the first mixture to a desired pH, such as 6.

In some embodiments, the oxidized carbon nanotubes can be extracted from the first mixture by drying the first mixture in a vacuum oven. The second mixture can be heated. The second mixture can be dissolved in tetrahydrofuran. The carbon nanotubes grafted with poly(citric acid) can be purified by precipitating the second mixture in cyclohexane.

In some embodiments, the carbon nanotubes grafted with poly(citric acid), 4-(dimethylamino)pyridine, and N-(3-dimethylaminopropyl)-N'-ethylcarbodiimide hydrochloride can be dissolved in anhydrous dimethylformamide in the third mixture.

In some embodiments, anhydrous dimethylformamide that comprises the drug can be added to the third mixture to synthesize the carbon nanotubes grafted with poly(citric acid) and the drug in the fourth mixture. A mixture that comprises paclitaxel can be added to the third mixture to synthesize the carbon nanotubes grafted with poly(citric acid) and paclitaxel in the fourth mixture. The mixture that comprises the drug can be stirred with the third mixture for 24 hours to synthesize the carbon nanotubes grafted with poly(citric acid) and the drug in the fourth mixture.

In some embodiments, the range of the weight ratio of the carbon nanotubes grafted with poly(citric acid) to the drug can be 0.1:1 to 2:1, or, preferably, 1:1.

In some embodiments, the drug can be conjugated to the carbon nanotubes grafted with poly(citric acid) via a cleavable ester bond in the fourth mixture. The fourth mixture can be dried under nitrogen steam.

In some embodiments, a method for synthesizing carbon nanotube drug carriers including oxidizing carbon nanotubes in a first mixture, mixing the oxidized carbon nanotubes and monohydrated citric acid to synthesize carbon nanotubes grafted with poly(citric acid) in a second mixture, and adding a mixture that comprises a drug to the second mixture to synthesize the carbon nanotubes grafted with poly(citric acid) and the drug.

Details of one or more implementations of the poly(citric acid) functionalized carbon nanotube drug delivery system are set forth in the accompanying drawings and the description below. Other aspects that can be implemented will be apparent from the description and drawings, and from the claims.

DETAILED DESCRIPTION

A process for synthesizing carbon nanotube drug carriers is disclosed. In particular, carbon nanotubes (hereinafter "CNTs") are initially functionalized to include (poly)citric acid ("PCA") branches, resulting in CNTs grafted with PCA ("CNTs-g-PCA"). Next, a drug, such as, for example, paclitaxel, can be conjugated to the CNTs-g-PCA via a cleavable ester bond, resulting in CNTs-g-PCA and paclitaxel ("CNTs-g-PCA-PTX"). As discussed in greater detail below, cytotoxicity studies reveal that CNTs-g-PCA-PTX increase the cytotoxic effect of paclitaxel.

Figure 1A:
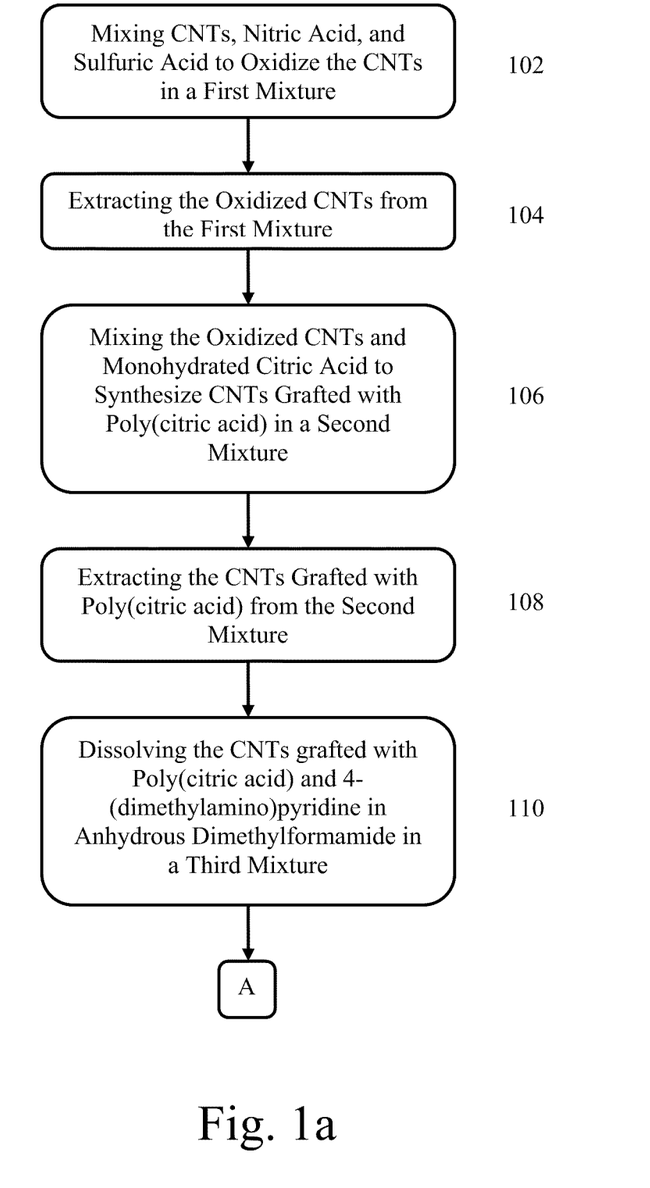
FIGS. 1a-b are flowcharts of an example of a process for synthesizing poly(citric acid) functionalized carbon nanotube drug carriers.
Figure 1B:
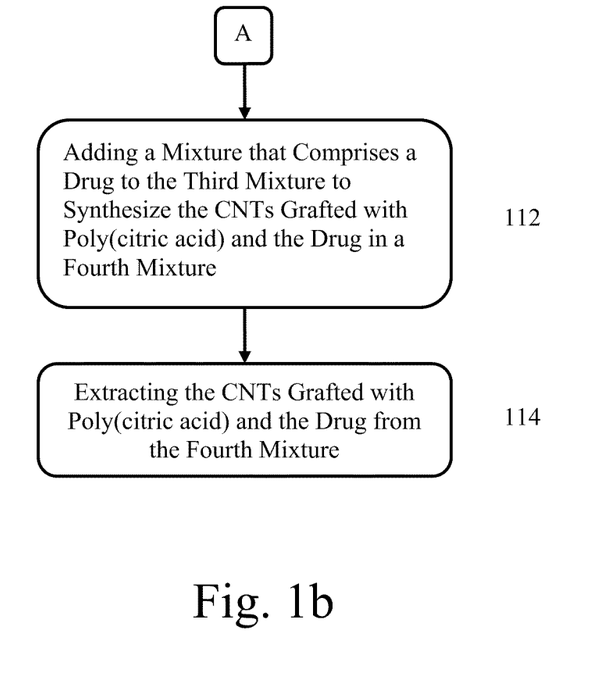

Referring to FIGS. 1a-b, an example of a process for synthesizing poly(citric acid) functionalized carbon nanotube drug carriers is illustrated. Initially, CNTs, nitric acid ($HNO_3$), and sulfuric acid ($H_2SO_4$) are mixed to oxidize the CNTs in a first mixture (step 102). The CNTs can be, for example, single-walled CNTs and/or multi-walled CNTs. Multi-walled CNTs can have 3 to 15 walls, an outer diameter of 5 to 20 nm, and a length of 1 to 10 μm. The nitric acid ($HNO_3$) and the sulfuric acid ($H_2SO_4$) can be mixed at a 1:3 ratio. For example, in some embodiments, 1 g of multi-walled CNTs can be mixed with 20 mL of nitric acid ($HNO_3$) and sulfuric acid ($H_2SO_4$) at a 1:3 ratio, i.e., about 5 mL of nitric acid ($HNO_3$) and about 15 mL of sulfuric acid ($H_2SO_4$).

The mixture of CNTs, nitric acid ($HNO_3$), and sulfuric acid ($H_2SO_4$) can be sonicated, i.e., applying sound, such as ultrasound, energy to agitate particles in the mixture, for about 30 minutes and refluxed for about 24 hours at 100° C. The resultant mixture can then be diluted with 1 L of distilled water, filtered, and washed with deionized water to adjust the pH of the mixture to 6.

Figure 2:
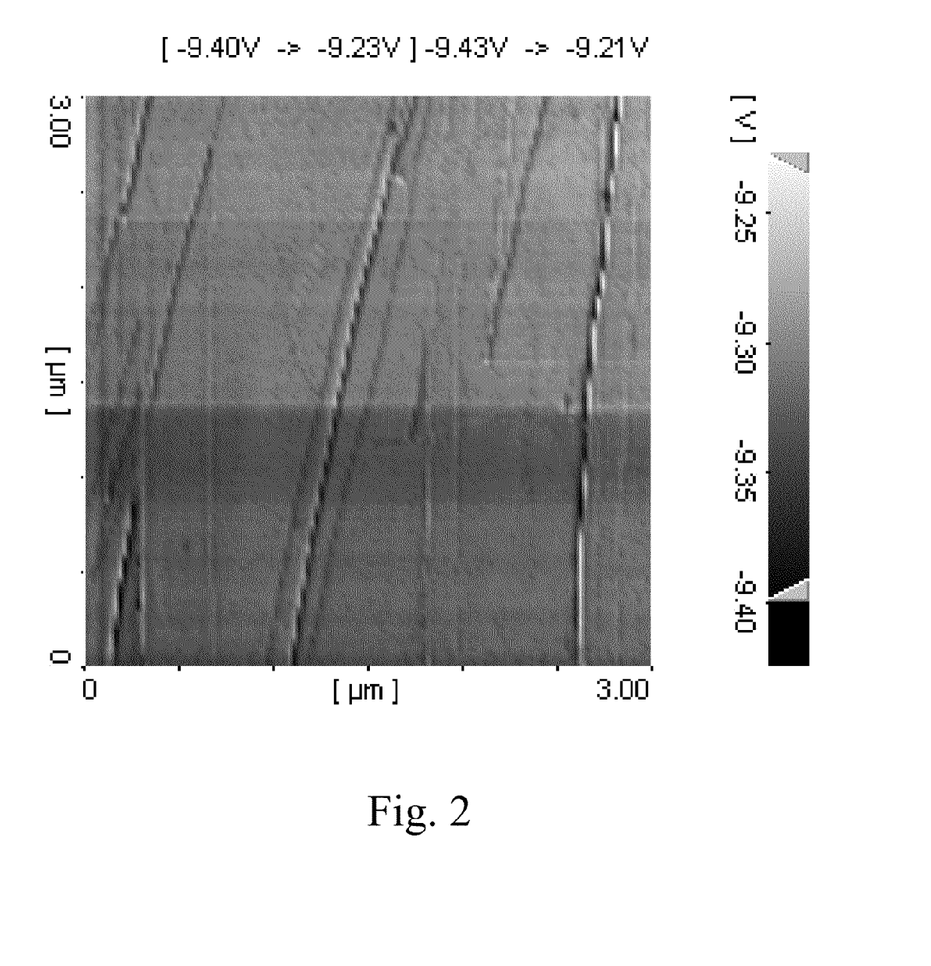
FIG. 2 illustrates an atomic force microscopy image of example oxidized carbon nanotubes on a mica surface.

Next, the oxidized CNTs can be extracted from the first mixture (step 104). The filtrate resulting from step 102 can be dried in a vacuum oven for about 24 hours at 40° C. to extract the oxidized CNTs. FIG. 2 illustrates an atomic force microscopy image of example oxidized CNTs on a mica surface imaged in air under ambient conditions. As illustrated in FIG. 2, the oxidized CNTs are linear or fiber-shaped.

The oxidized CNTs and monohydrated citric acid are mixed to synthesize CNTs grafted with poly(citric acid) ("CNTs-g-PCA") in a second mixture (step 106). In some embodiments, 0.1 g of oxidized CNTs and 2.5 g of monohydrated citric acid can be added to a polymerization ampoule equipped with a magnetic stirrer and a vacuum inlet. The second mixture can be heated to 100° C. while being stirred for 30 minutes. Then, the temperature of the second mixture can be gradually increased to 140° C. over a time period of 4 hours while a dynamic vacuum is operated at proper intervals to remove the water from the second mixture. The resulting product can then be cooled and dissolved in tetrahydrofuran.

Next, the CNTs-g-PCA can be extracted from the second mixture (step 108). In some embodiments, the CNTs-g-PCA are purified by precipitating the second mixture in cyclohexane to extract the free citric acid, leaving the purified CNTs-g-PCA in tetrahydrofuran.

Figure 3A:
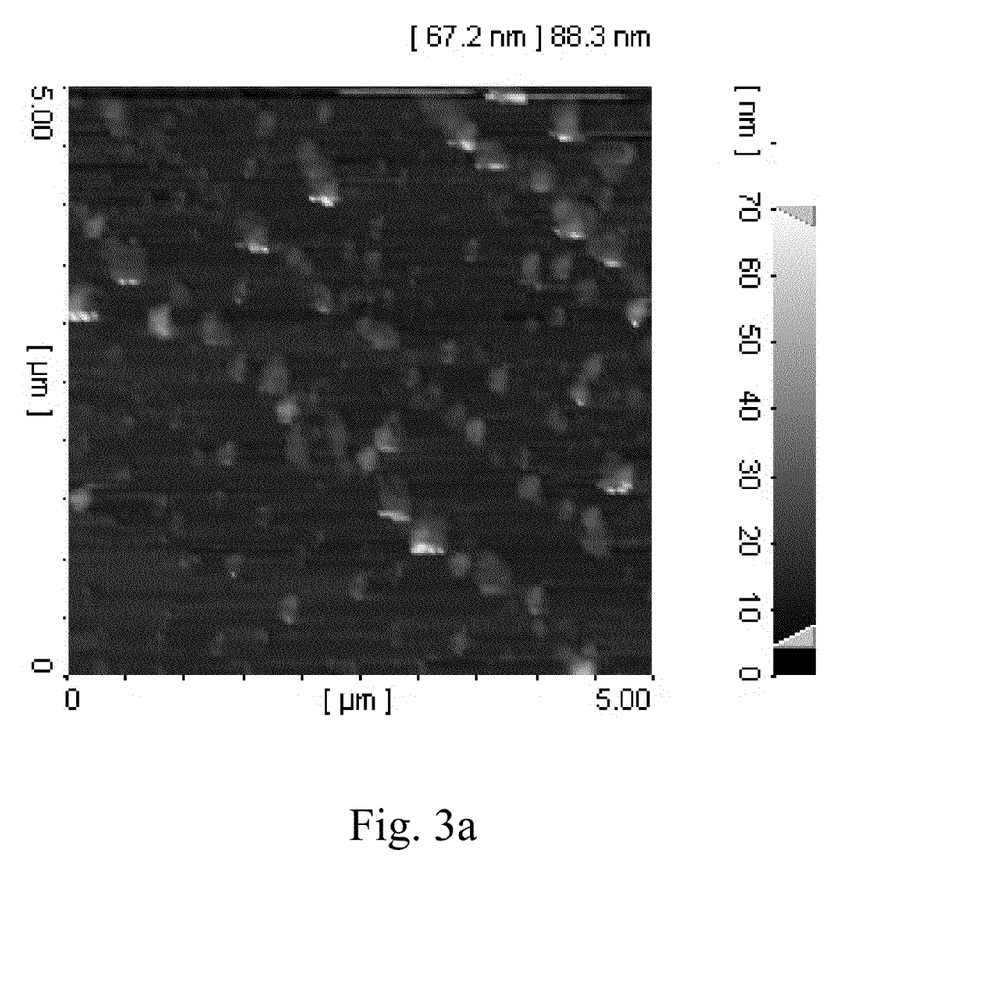
FIGS. 3a-b illustrate atomic force microscopy images of example carbon nanotubes grafted with poly(citric acid) on a mica surface.
Figure 3B:
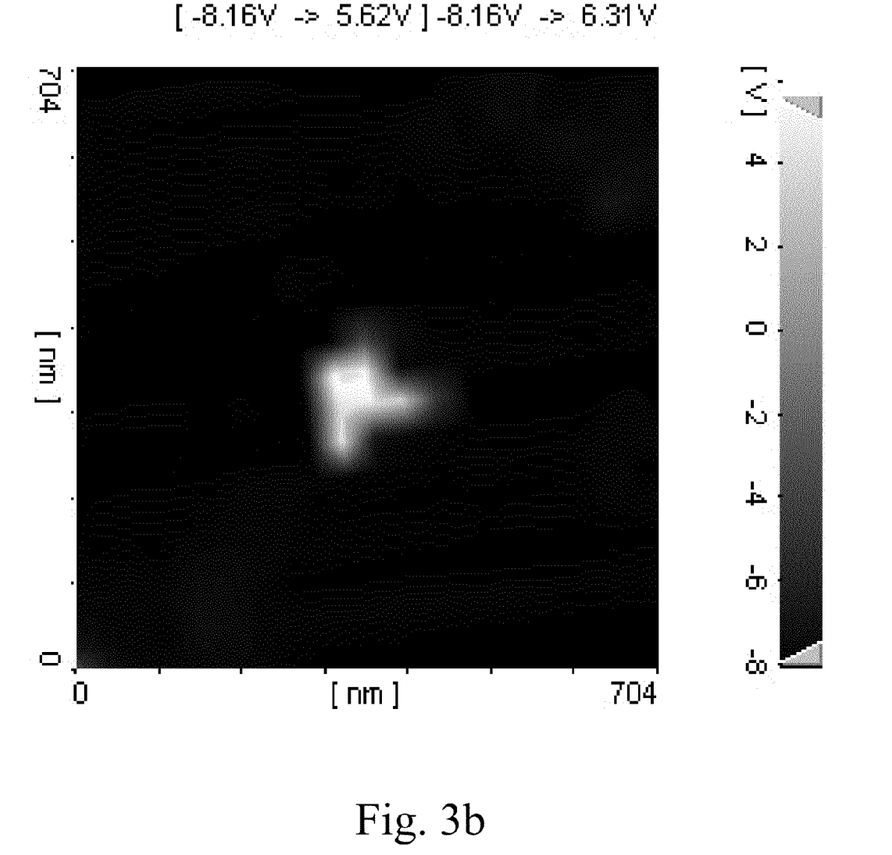

Poly(citric acid) is a highly hydrophilic polymer and, as such, it decreases the natural hydrophobicity of CNTs, such that, to decrease the interaction between the CNTs and water molecules, CNTs-g-PCA in aqueous solution adapts to a curved conformation in which the CNTs have the lowest interaction with the solvent. Therefore, the straight or linear conformation of the oxidized CNTs changes to a curved conformation for CNTs-g-PCA. For example, FIGS. 3a-b illustrate atomic force microscopy images of example CNTs-g-PCA on a mica surface imaged in air under ambient conditions. As illustrated in FIGS. 3a-b, the CNTs-g-PCA have a curved or spherical morphology and a size of approximately 125 to 150 nm.

Poly(citric acid) is also a highly functional polymer with a large number of hydroxyl functional groups that confer a high loading capacity to the CNTs. In addition, poly(citric acid) is a highly biocompatible polymer. Due to at least these properties of poly(citric acid), CNTs-g-PCA are excellent drug carriers.

The CNTs-g-PCA and 4-(dimethylamino)pyridine are dissolved in anhydrous dimethylformamide in a third mixture (step 110). In some embodiments, the third mixture can also include N-(3-dimethylaminopropyl)-N'-ethylcarbodiimide hydrochloride. For example, in some embodiments, 50 mg of CNTs-g-PCA, 23 mg of N-(3-dimethylaminopropyl)-N'-ethylcarbodiimide hydrochloride, which is equivalent to 0.12 millimoles of N-(3-dimethylaminopropyl)-N'-ethylcarbodiimide hydrochloride, and 15 mg of 4-(dimethylamino)pyridine, which is equivalent to 0.12 millimoles of 4-(dimethylamino)pyridine, can be dissolved in 5 mL of anhydrous dimethylformamide. The third mixture can be stirred, for example, for 30 minutes at 0° C.

Figure 4:
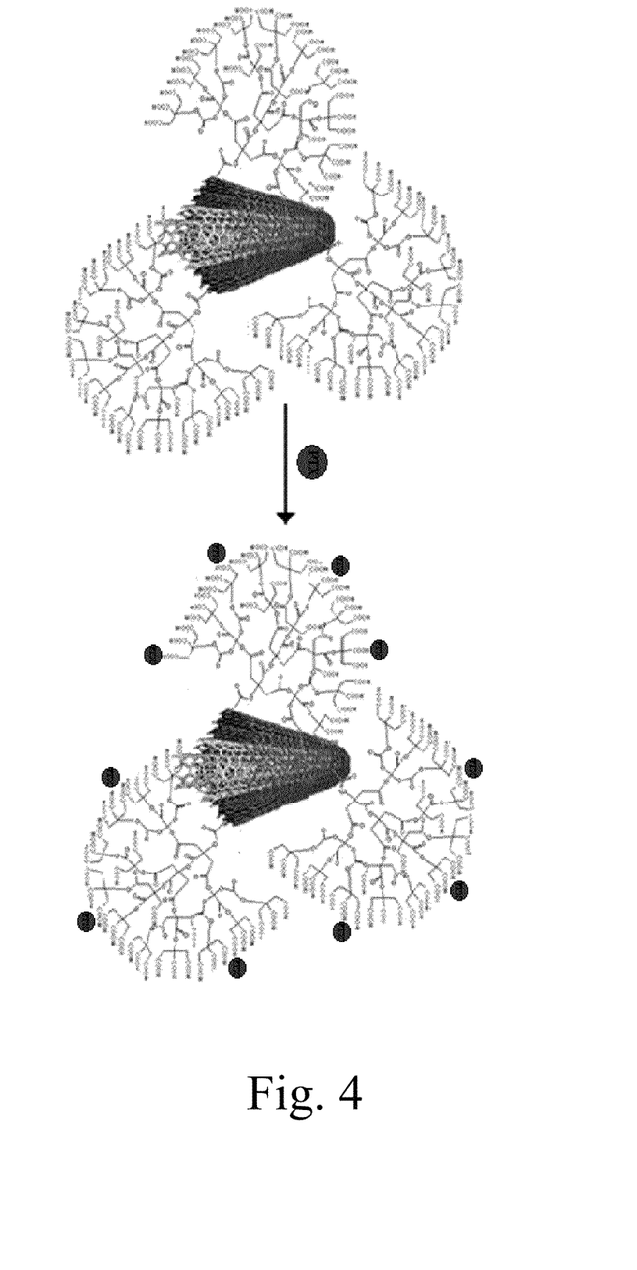
FIG. 4 illustrates an example illustration of paclitaxel conjugating with a carbon nanotube grafted with poly(citric acid).

Next, a mixture that comprises a drug can be added to the third mixture to synthesize the CNTs-g-PCA and the drug in a fourth mixture (step 112). In some embodiments the mixture that comprises the drug can be anhydrous dimethylformamide comprising the drug. The drug can be, for example, paclitaxel ("PTX"). FIG. 4 illustrates an example illustration of paclitaxel conjugating with a CNTs-g-PCA.

For example, in some embodiments, 5 mL of anhydrous dimethylformamide containing 50 mg of paclitaxel, which is equivalent to 0.06 millimoles of paclitaxel, can be added to the third mixture and stirred for 24 hours at 0° C. Under these conditions, the percentage of loaded paclitaxel is 38±7% and the reaction yield is 25±2%.

In some embodiments, the anhydrous dimethylformamide containing paclitaxel and the third mixture can be stirred for 48 hours, while in other embodiments, the anhydrous dimethylformamide containing paclitaxel and the third mixture can be stirred for 72 hours. In some embodiments, the anhydrous dimethylformamide can contain 5 mg, 25 mg, or 100 mg of paclitaxel. As such, the weight ratio of CNTs-g-PCA to paclitaxel can range from 0.1:1 to 2:1.

The resulting precipitate can be filtered and the filtrate can be dialyzed against anhydrous dimethylformamide for 18 to 20 hours to remove the unconjugated drug, such as, for example, the unconjugated paclitaxel. The paclitaxel is covalently loaded on the surface of CNTs-g-PCA by conjugating to the carboxyl functional groups of the poly(citric acid) branches on the surface of CNTs via a cleavable ester bond. As a result, CNTs grafted with poly(citric acid) and paclitaxel ("CNTs-g-PCA-PTX") are synthesized.

Figure 5A:
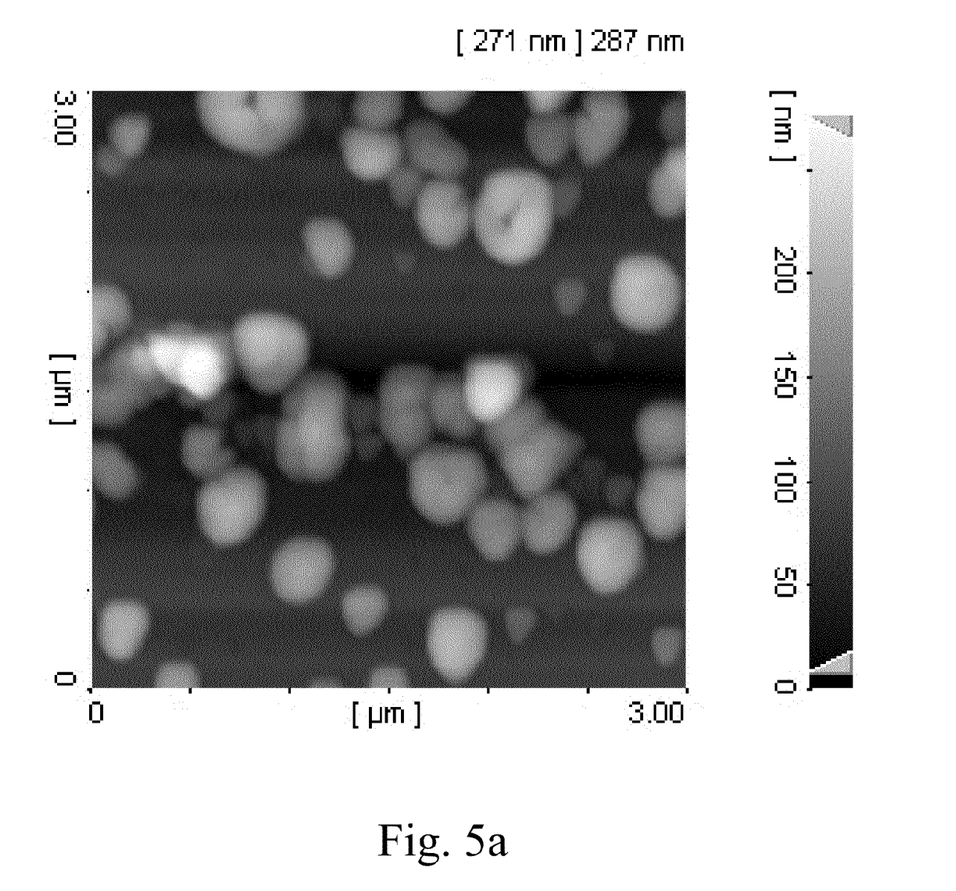
FIGS. 5a-c illustrate atomic force microscopy images of example carbon nanotubes grafted with poly(citric acid) and paclitaxel on a mica surface.
Figure 5B:
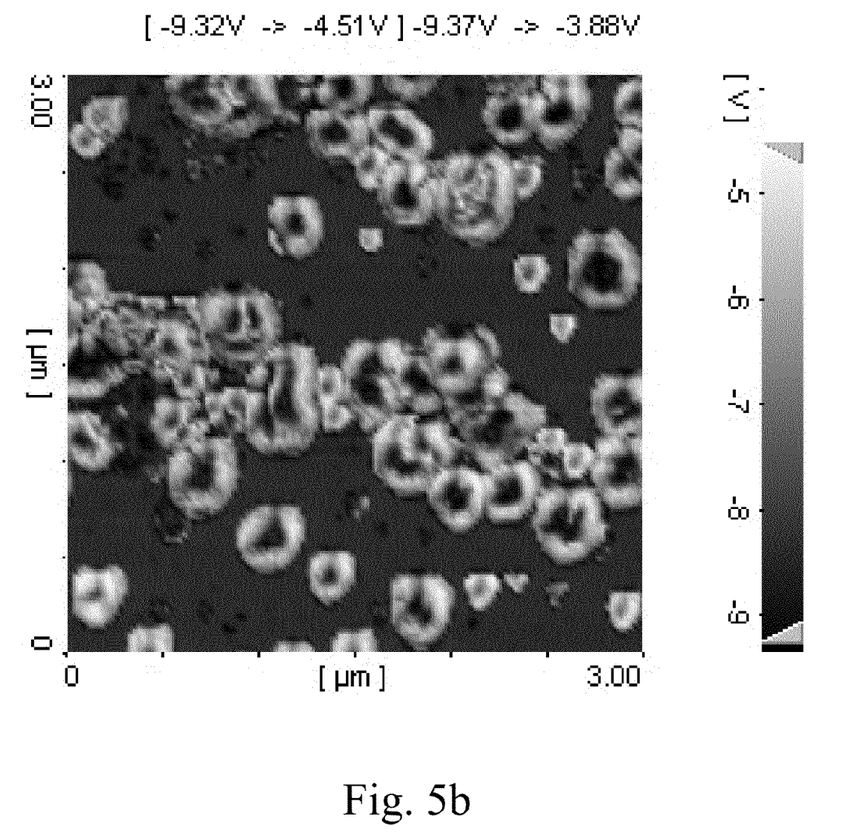
Figure 5C:
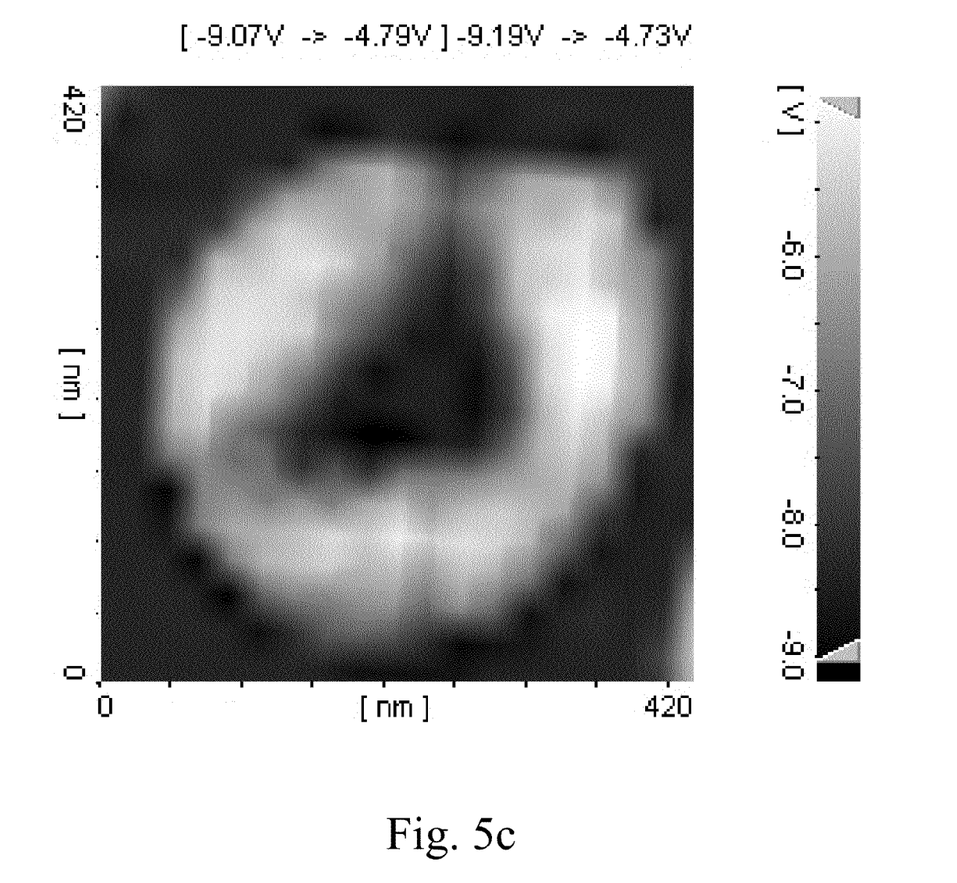
Figure 6A:
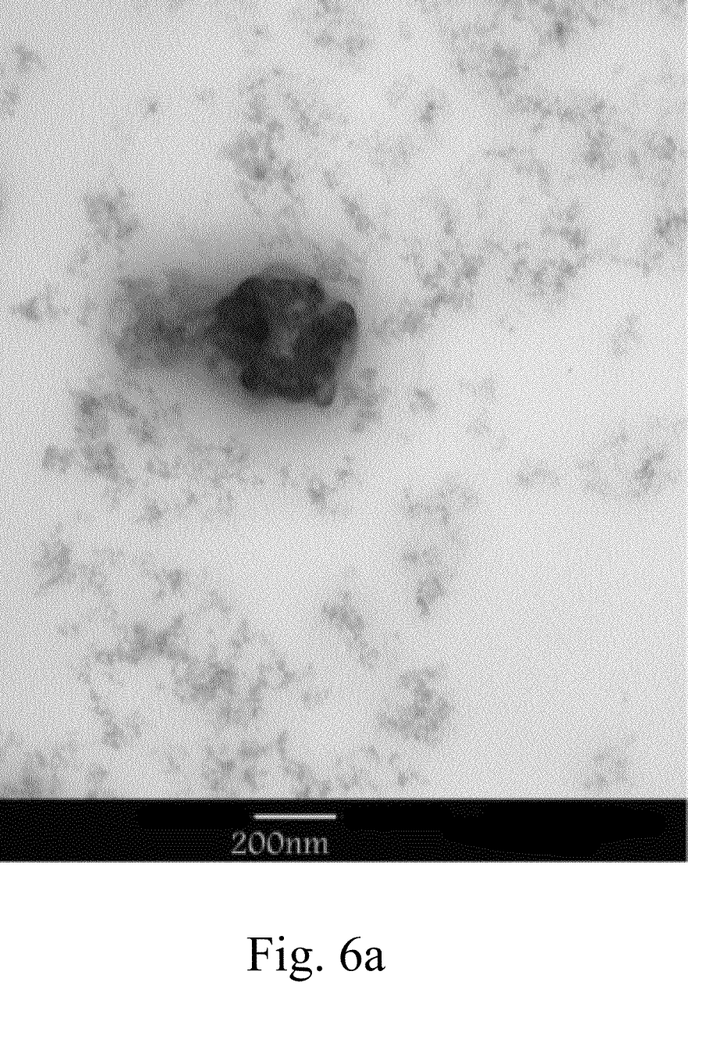
FIGS. 6a-b illustrate transmission electron microscopy images of example carbon nanotubes grafted with poly(citric acid) and paclitaxel.
Figure 6B:
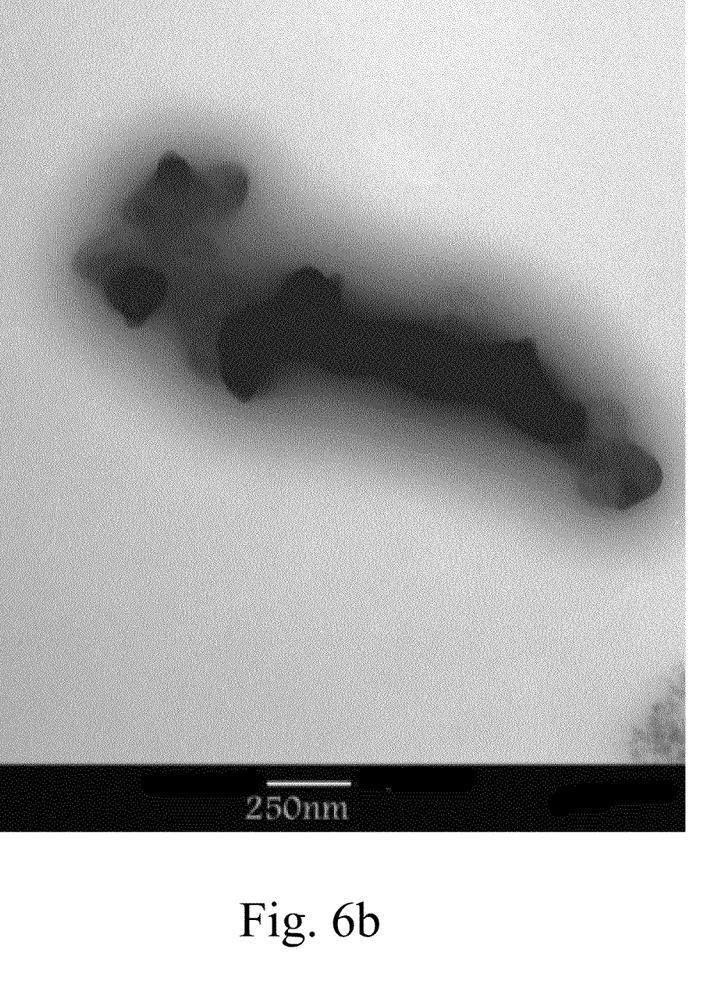

Finally, the CNTs grafted with poly(citric acid) and the drug, such as, for example, CNTs-g-PCA-PTX, are extracted from the fourth mixture (step 114). For example, in some embodiments, the fourth mixture can be dried under nitrogen stream for 4 hours. FIGS. 5a-c illustrate atomic force microscopy images of example CNTs-g-PCA-PTX on a mica surface imaged in air under ambient conditions. FIGS. 6a-b show transmission electron microscopy images of example CNTs-g-PCA-PTX imaged at 100 kV. As illustrated, the CNTs-g-PCA-PTX nanoparticles in FIGS. 5a-c and 6a-b have curved and/or spherical conformations.

Figure 7:
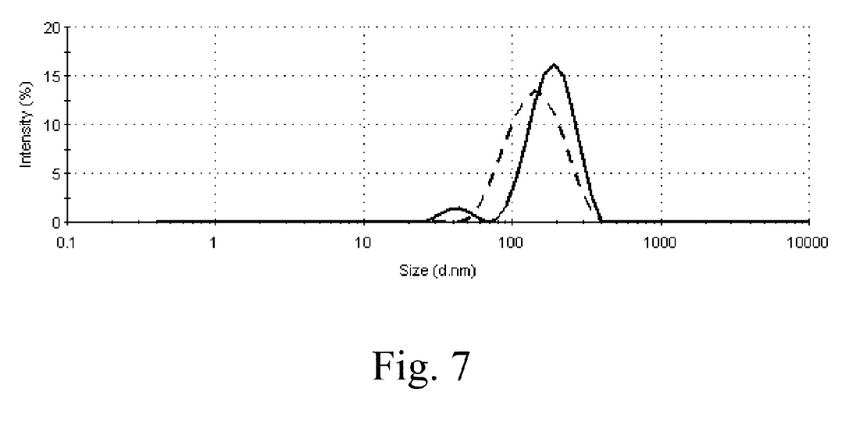
FIG. 7 illustrates a chart showing the size of carbon nanotubes grafted with poly(citric acid) and carbon nanotubes grafted with poly(citric acid) and paclitaxel evaluated using dynamic light scattering.

In addition to atomic force microscopy and transmission electron microscopy, the sizes of the CNTs-g-PCA and CNTs-g-PCA-PTX were also evaluated using dynamic light scattering at 25° C. Referring to FIG. 7, as shown by the dashed line, the size of CNTs-g-PCA in water is about 125 nm, which is much less than the 1 to 10 μm of the starting multi-walled CNTs. The decrease in length of CNTs after being grafted with poly(citric acid) is due to the hydrophobicity of CNTs and hydrophilicity of poly(citric acid) in aqueous solutions, causing poly(citric acid) branches to surround the CNTs to form curved or spherical CNTs. As shown by the solid line in FIG. 7, the size of CNTs-g-PCA-PTX is about 207 nm, suggesting no significant aggregation of the CNTs-g-PCA after conjugation of the paclitaxel molecules.

Referring back to FIGS. 5a-c and 6a-b, the atomic force microscopy images and transmission electron microscopy images of CNTs-g-PCA-PTX show a spherical nanostructure having a diameter of about 350 nm, which is significantly greater than the 207 nm size measured as a result of dynamic light scattering. However, the size of each CNTs-g-PCA-PTX alone is about the same size as obtained using dynamic light scattering, thereby indicating that the larger size of CNTs-g-PCA-PTX in the atomic force microscopy images is due to aggregation. The aggregation is due to the solvent evaporation that occurs during sample preparation for atomic force imaging and transmission electron microscopy imaging, causing aggregation of the CNTs-g-PCA-PTX, and producing larger nanoparticles.

In vitro cytotoxicity experiments were conducted on SKOV3 ovarian cancer cells and A549 lung cancer cells. The cytotoxicity of CNTs-g-PCA-PTX and free paclitaxel was assessed by MTT (3-(4,5-Dimethylthiazol-2-yl)-2,5-diphenyltetrazolium bromide) assays. The SKOV3 ovarian cancer cells and the A549 lung cancer cells were cultured in a RPMI-1640 medium supplemented with 10% fetal bovine serum and 1% penicillin-streptomycin at 37° C. in a humidified incubator with 5% carbon dioxide ($CO_2$). The cells were seeded in 96-well plates at a density of $1 \times 10^4$ viable cells per well. After overnight incubation, the cells were exposed with different concentrations of free paclitaxel and CNTs-g-PCA-PTX in dimethyl sulfoxide at 37° C. for predetermined time intervals. At designated time intervals, such as, for example, 24 hours, 20 μL of MTT with a concentration of 5 mg/mL was added to each well and the well plates were incubated for 3 to 4 hours. Formazan crystals in each well were then dissolved with 100 μL of dimethyl sulfoxide and the absorbance of each well was measured with a microplate reader at 570 nm. The percentage of cell viability was calculated according to following equation:

$$\text{Cell viability percentage} = \frac{\text{Absorbance at 570 nm of treated group}}{\text{Absorbance at 570 nm of control group}} \times 100$$

Figure 8A:
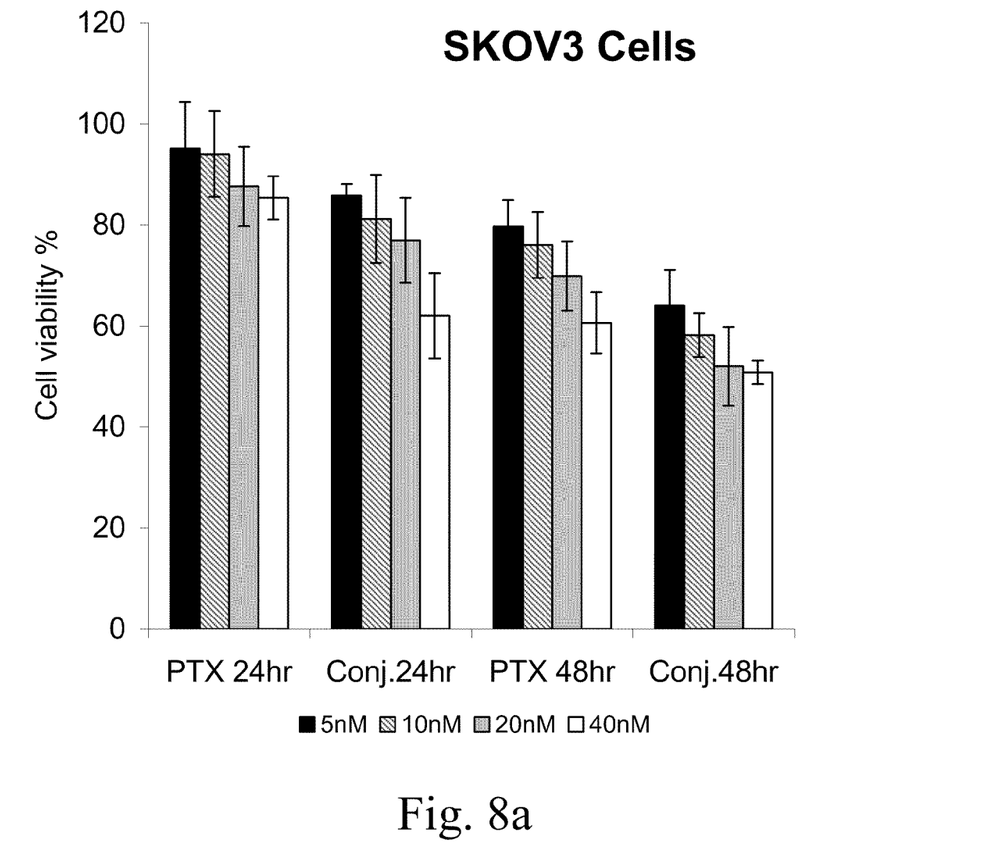
FIGS. 8a-b illustrate graphs showing the cell viability percentage of SKOV3 cells and of A549 cells, respectively.
Figure 8B:
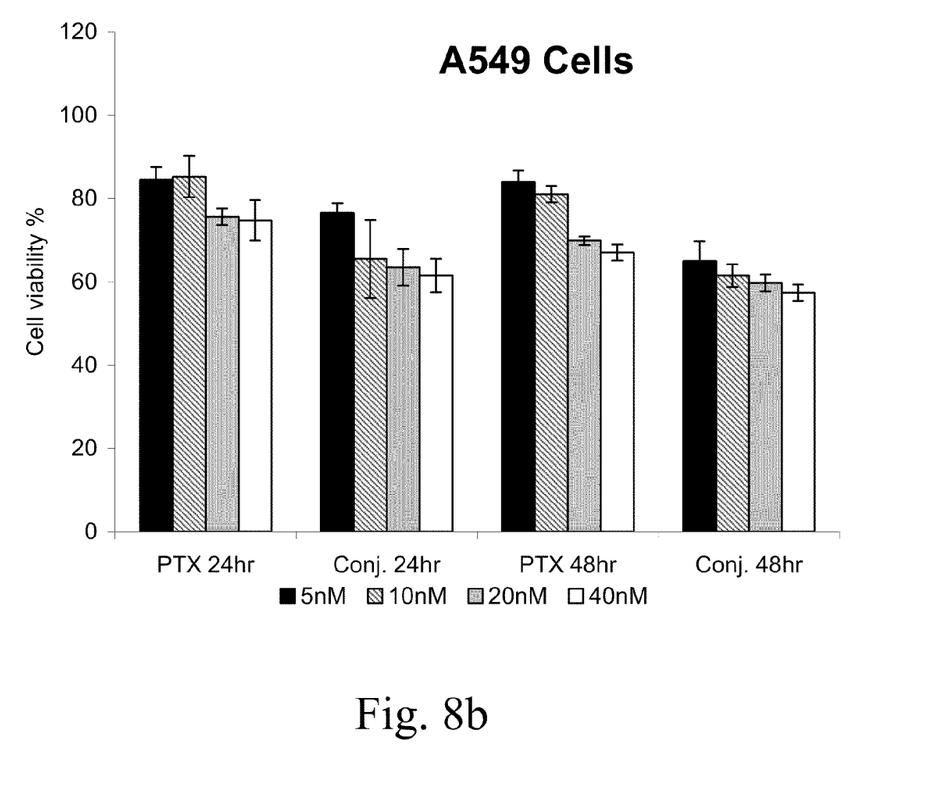

FIG. 8a shows the cell viability percentage of SKOV3 cells and FIG. 8b shows the cell viability of A549 cells incubated with free paclitaxel and CNTs-g-PCA-PTX at paclitaxel concentrations of 5 nM (solid black column), 10 nM (striped column), 20 nM (gray column), and 40 nM (white column) for 24 hours and 48 hours.

Generally, as illustrated in FIG. 8a, CNTs-g-PCA-PTX showed the same cytotoxic effect as free paclitaxel at much lower concentrations of paclitaxel. For example, referring to FIG. 8a, the cytotoxic effect of CNTs-g-PCA-PTX containing 5 nM of paclitaxel was equal to the cytotoxic effect of 40 nM free paclitaxel in SKOV3 cells after 24 hours. In addition, at constant paclitaxel concentrations, CNTs-g-PCA-PTX exhibited the same cytotoxic effect as free paclitaxel after shorter incubation times. As shown in FIG. 8a, for example, at 40 nM concentration, the cytotoxicity of CNTs-g-PCA-PTX after 24 hours was equal to the cytotoxicity of free paclitaxel after 48 hours. Therefore, CNTs-g-PCA-PTX exhibits a greater cytotoxic effect in comparison with free paclitaxel after a shorter period of time. Similar results are observed in the case of A549 cells, as illustrated in FIG. 8b. As such, CNTs-g-PCA-PTX can be considered an effective delivery system for cancer chemotherapy.

These results can be due to the increased cell penetration of paclitaxel when conjugated to CNTs-g-PCA. The increased cell penetration of CNTs-g-PCA-PTX is an outcome of (1) the hydrophilicity of CNTs-g-PCA-PTX, leading to relatively better interaction with cell walls than free, hydrophobic paclitaxel; (2) the spherical conformation of CNTs-g-PCA-PTX; and (3) the presence of CNTs as the backbone of the conjugates, as it has been determined that CNT nanocarriers are effective in penetrating various cells.

It is to be understood the implementations are not limited to the particular devices or apparatus described which may, of course, vary. It is also to be understood that the terminology used herein is for the purpose of describing particular implementations only, and is not intended to be limiting. As used in this specification, the singular forms "a", "an" and "the" include plural referents unless the content clearly indicates otherwise.

Accordingly, other implementations are within the scope of this application.

What is claimed is:

1. A method for synthesizing carbon nanotube drug carriers, comprising:
   mixing carbon nanotubes and at least one acid to oxidize the carbon nanotubes;
   mixing the oxidized carbon nanotubes and monohydrated citric acid to synthesize carbon nanotubes grafted with poly(citric acid);
   mixing the carbon nanotubes grafted with poly(citric acid) with a mixture comprising 4-(dimethylamino)pyridine and N-(3-dimethylaminopropyl)-N'-ethylcarbodiimide hydrochloride; and
   adding a mixture comprising anhydrous dimethylformamide and a drug to the mixture of the carbon nanotubes grafted with poly(citric acid), 4-(dimethylamino)pyridine, and N-(3-dimethylaminopropyl)-N'-ethylcarbodiimide hydrochloride to synthesize carbon nanotubes grafted with poly(citric acid) and the drug, wherein:
   the weight ratio of the carbon nanotubes grafted with poly(citric acid) to the drug is between 0.1:1 and 2:1, and
   the carbon nanotubes grafted with poly(citric acid) and the drug have a curved conformation.

2. The method of claim 1, wherein mixing the carbon nanotubes and the at least one acid to oxidize the carbon nanotubes comprises mixing the carbon nanotubes, nitric acid, and sulfuric acid to oxidize the carbon nanotubes.

3. The method of claim 1, wherein mixing the carbon nanotubes and the at least one acid to oxidize the carbon nanotubes comprises sonicating the carbon nanotubes and the at least one acid.

4. The method of claim 1, wherein the carbon nanotubes are multi-walled carbon nanotubes.

5. The method of claim 1, further comprising extracting the oxidized carbon nanotubes by drying the oxidized carbon nanotubes.

6. The method of claim 1, wherein mixing the oxidized carbon nanotubes and the monohydrated citric acid to synthesize the carbon nanotubes grafted with poly(citric acid)

comprises heating the oxidized carbon nanotubes and the monohydrated citric acid to synthesize the carbon nanotubes grafted with poly(citric acid).

7. The method of claim 1, wherein mixing the oxidized carbon nanotubes and the monohydrated citric acid to synthesize the carbon nanotubes grafted with poly(citric acid) comprises dissolving the oxidized carbon nanotubes and the monohydrated citric acid in tetrahydrofuran.

8. The method of claim 1, further comprising extracting the carbon nanotubes grafted with poly(citric acid) by precipitating the carbon nanotubes grafted with poly(citric acid) in cyclohexane.

9. The method of claim 1, wherein the drug is paclitaxel.

10. The method of claim 1, wherein adding the mixture comprising anhydrous dimethylformamide and the drug to the mixture of the carbon nanotubes grafted with poly(citric acid), 4-(dimethylamino)pyridine, and N-(3-dimethylaminopropyl)-N'-ethylcarbodiimide hydrochloride to synthesize the carbon nanotubes grafted with poly(citric acid) and the drug comprises stirring the mixture comprising anhydrous dimethylformamide and the drug with the mixture of the carbon nanotubes grafted with poly(citric acid), 4-(dimethylamino)pyridine, and N-(3-dimethylaminopropyl)-N'-ethylcarbodiimide hydrochloride for at least 24 hours to synthesize the carbon nanotubes grafted with poly(citric acid) and the drug.

11. The method of claim 1, wherein adding the mixture comprising anhydrous dimethylformamide and the drug to the mixture of the carbon nanotubes grafted with poly(citric acid), 4-(dimethylamino)pyridine, and N-(3-dimethylaminopropyl)-N'-ethylcarbodiimide hydrochloride to synthesize the carbon nanotubes grafted with poly(citric acid) and the drug comprises adding the mixture comprising anhydrous dimethylformamide and the drug to the mixture of the carbon nanotubes grafted with poly(citric acid), 4-(dimethylamino)pyridine, and N-(3-dimethylaminopropyl)-N'-ethylcarbodiimide hydrochloride so that the drug is conjugated to the carbon nanotubes grafted with poly(citric acid) via a cleavable ester bond.

12. The method of claim 1, further comprising extracting the carbon nanotubes grafted with poly(citric acid) and the drug by drying the carbon nanotubes grafted with poly(citric acid) and the drug.

13. The method of claim 1, further comprising applying the carbon nanotubes grafted with poly(citric acid) and the drug to living cells.

* * * * *